(12) United States Patent
Wakimura et al.

(10) Patent No.: US 7,041,853 B2
(45) Date of Patent: May 9, 2006

(54) PROCESS FOR PRODUCING 4-BROMOTHIOANISOLE

(75) Inventors: Kenichi Wakimura, Kako-gun (JP); Hitoshi Karino, Kako-gun (JP); Hirokazu Kagano, Kako-gun (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 61 days.

(21) Appl. No.: 10/239,077

(22) PCT Filed: Mar. 21, 2001

(86) PCT No.: PCT/JP01/02220

§ 371 (c)(1),
(2), (4) Date: Mar. 25, 2003

(87) PCT Pub. No.: WO01/70680

PCT Pub. Date: Sep. 27, 2001

(65) Prior Publication Data

US 2003/0166971 A1 Sep. 4, 2003

(30) Foreign Application Priority Data

Mar. 21, 2000 (JP) .................. 2000-077561

(51) Int. Cl.
*C07C 321/26* (2006.01)

(52) U.S. Cl. .............. 568/306; 568/18; 568/38
(58) Field of Classification Search ............ 568/18, 568/38, 56, 306
See application file for complete search history.

(56) References Cited

FOREIGN PATENT DOCUMENTS

| JP | 3-181455 | 8/1991 |
| JP | 5-140086 | 6/1993 |

OTHER PUBLICATIONS

CA:123:340603 abs of Journal of Chem Soc Perkin Trans 2 by Davies et al (7) pp 1287–94 1995.*
J Org Chem by Bohra et al pp. 3562–3567 vol. 62 1997.*
R. Breslow et al, Cabonium Ions With Multiple Neighboring Groups. I. Synthesis, Journal of the American Chemical Society, 1968, pp. 4051–4055, vol. 90, No. 15, XP002301405.

* cited by examiner

*Primary Examiner*—Samuel Barts
*Assistant Examiner*—Lansana Nyalley
(74) *Attorney, Agent, or Firm*—Sughrue Mion, PLLC

(57) ABSTRACT

It is an object of the present invention to provide a process for producing highly pure 4-bromothioanisole, which is useful in the manufacture of medicinal chemicals, agrochemicals or functional materials, in a simple and industrially advantageous manner.

The present invention is related to a process for producing 4-bromothioanisole
which comprises adding an alcoholic solvent to a 4-bromothioanisole-containing product resulting from the reaction of thioanisole with bromine to cause crystallization of 4-bromothioanisole.

4 Claims, No Drawings

PROCESS FOR PRODUCING 4-BROMOTHIOANISOLE

TECHNICAL FIELD

The present invention relates to a process for producing 4-bromothioanisole. More particularly, it relates to a process for producing 4-bromothioanisole, which is a useful compound used in various fields such as medicinal chemicals, agrochemicals and functional materials.

BACKGROUND ART

Methods are known for the production of 4-bromothioanisole, for example, (1) the method comprising reacting thioanisole with bromine, followed by purification using a flash column (J. Amer. Chem. Soc., 119, 11381 (1997)), and (2) the method comprising reacting p-dibromobenzene with methanethiol copper salt (J. Amer. Chem. Soc., 90, 4051 (1968)).

As for method (1), however, it is difficult to separate the desired product 4-bromothioanisole from the byproduct 2-bromothioanisole, hence the purity of the desired product is low. As regards method (2), the yield is low, and copper-containing wastewater is generated, producing an environmental problem.

SUMMARY OF THE INVENTION

It is an object of the present invention to provide a process for producing highly pure 4-bromothioanisole, which is useful in the manufacture of medicinal chemicals, agrochemicals or functional materials, in a simple and industrially advantageous manner.

The present invention provides a process for producing 4-bromothioanisole which comprises adding an alcoholic solvent to a 4-bromothioanisole-containing product resulting from the reaction of thioanisole with bromine to cause crystallization of 4-bromothioanisole.

The amount of addition of the alcoholic solvent is preferably 0.03 to 10 times the weight of 4-bromothioanisole.

The alcoholic solvent is preferably a lower alcohol or a mixed solvent composed of a lower alcohol and water.

The lower alcohol is preferably methanol.

DETAILED DISCLOSURE OF THE INVENTION

The present inventors made intensive investigations to solve the above problems and, as a result, found that highly pure 4-bromothioanisole can be produced in a commercially advantageous manner when an alcoholic solvent is added to the 4-bromothioanisole obtainable by reacting thioanisole with bromine and the product is caused to crystallize out. Based on this finding, they have completed the present invention.

In the practice of the present invention, 4-bromothioanisole is first produced. The process for producing 4-bromothioanisole is not particularly restricted but, among others, the process comprising reacting thioanisole with bromine in the presence of a Lewis acid catalyst is preferably used.

The Lewis acid catalyst is not particularly restricted but includes, among others, iron(II) chloride, aluminum chloride, boron trifluoride, zinc chloride, iron, magnesium chloride and samarium chloride. Among them, iron(II) chloride, aluminum chloride and boron trifluoride are preferred from economical points of view.

The Lewis acid catalyst is used in an amount of 0.001 to 5.0 mole percent, preferably 0.005 to 2.0 mole percent, relative to thioanisole. When the amount of the Lewis acid catalyst is smaller than 0.001 mole percent, any substantial effect of addition of the catalyst will not be produced. Conversely, when it exceeds 5.0 mole percent, the effect will no more proportional to the addition level and this is economically disadvantageous.

Bromine is used in an amount of 0.5 to 2 moles, preferably 0.5 to 1.5 moles, and more preferably 0.5 to 1.4 moles, per mole of thioanisole. When the amount of bromine is smaller than 0.5 moles per mole of thioanisole, the reaction possibly will not be driven to completion, leading to a decreased yield. Conversely, when it exceeds 2 moles per mole of thioanisole, the extra amount will not produce any additional effect and this is uneconomical.

The reaction is carried out at a temperature of −50° C. to 200° C., preferably −10° C. to 100° C. At a reaction temperature below −50° C., the rate of reaction is slow and a long period of time is required for completing the reaction. At above 200° C., side reactions may occur and the yield and purity may possibly decrease. The reaction time is generally 0.5 to 20 hours, although it may vary depending on the reaction temperature.

The above reaction can be carried out without using any solvent or with using a solvent. The solvent is not particularly restricted but includes, among others, hydrocarbons such as hexane, cyclohexane and heptane, halogenated hydrocarbons such as dichloroethane, dichloromethane and chloroform, and aromatic hydrocarbons such as benzene, toluene, xylene, chlorobenzene, dichlorobenzene and trichlorobenzene.

The amount of the above solvent is not particularly restricted but, generally, it is 0.1 to 10 times the weight of thioanisole. When the amount of the solvent exceeds 10 times the weight of thioanisole, the volume efficiency will unfavorably decline.

The invention is characterized in that an alcoholic solvent is added to the reaction mixture containing 4-bromothioanisole as obtained in the above manner to selectively cause 4-bromothioanisole to crystallize out in isolation from the byproduct 2-bromothioanisole to thereby give 4-bromothioanizole of high purity. As regards the process of adding the alcoholic solvent, the alcoholic solvent may be directly added to the reaction mixture containing 4-bromothioanisole to thereby obtain a crystal product of 4-bromothioanisole but, for more favorable results, the alcoholic solvent is added to the crude product 4-bromothioanisole obtained, for example, by removing the catalyst Lewis acid from the reaction mixture by washing with water. In cases where a solvent is used in carrying out the reaction, the alcoholic solvent may be added to the 4-bromothioanisole-containing reaction mixture after washing with water or the like treatment, as mentioned above, followed by causing crystallizing out. For better results, however, the alcoholic solvent is added to the crude product 4-bromothioanisole obtained by washing with water or the like treatment and distilling off the solvent.

The amount of addition of the above alcoholic solvent is 0.03 to 10 times, preferably 0.1 to 5 times, the weight of 4-bromothioanisole. When the amount of alcoholic solvent is smaller than 0.03 times the weight of 4-bromothioanisole, the purity of the product 4-bromothioanisole may possibly be low. Conversely, when it exceeds 10 times, the surplus amount added will not produce any additional effect; this is uneconomical.

The alcoholic solvent to be used in the practice of the present invention is not particularly restricted but may be, for example, a lower alcohol or a mixed solvent composed of a lower alcohol and water. Specific examples of the lower alcohol are methanol, ethanol, n-propyl alcohol and isopropyl alcohol, among others. Among them, methanol is preferably used.

The proportion of water in the lower alcohol-water mixed solvent is not particularly restricted but, generally, it is not more than 70% by weight, preferably not more than 50% by weight. When the amount of water exceeds 70% by weight, the purity of 4-bromothioanisole may possibly decrease.

In the practice of the present invention, the above-mentioned alcoholic solvent is added to crude 4-bromothioanisole and then the mixture is slowly cooled to thereby cause crystallization of 4-bromothioanisole. Generally, the mixture is cooled to a temperature of −20 to 30° C., preferably −10 to 20° C. When the cooling temperature is below −20° C., no corresponding extra effect can be produced and this is uneconomical. Conversely, at temperatures exceeding 30° C., 4-bromothioanisole hardly crystallizes out and the recovery rate may possibly decrease.

The thus-obtained 4-bromothioanisole is isolated in the conventional manner, for example, by filtration, and dried, whereby 4-bromothioanisole having a sufficiently high purity can be obtained. Furthermore, by washing the 4-bromothioanisole obtained with a cold lower alcohol and then drying the same, it is possible to obtain 4-bromothioanisole having a higher purity.

BEST MODES FOR CARRYING OUT THE INVENTION

The following examples illustrate the present invention in more detail. Those examples are, however, by no means limitative of the scope of the invention.

EXAMPLE 1

A one-liter four-necked flask equipped with a stirrer, thermometer, dropping funnel and Liebig condenser was charged with 124.2 g (1.00 mole) of thioanisole and 0.32 g (0.002 mole) of iron(II) chloride, and 160 g (1.0 mole) of bromine was added dropwise with stirring at 50° C. over 4 hours. Thereafter, the reaction was further allowed to proceed for 1 hour. After completion of the reaction, 50 g of water was added, and the organic layer was separated, whereby 202.9 g of crude 4-bromothioanisole was obtained. The purity of the thus-obtained crude 4-bromothioanisole was 90.3% as determined by gas chromatography.

Methanol (200.0 g) was added to the crude 4-bromothioanisole obtained, and the mixture was slowly cooled from 50° C. to −5° C. with stirring to thereby cause 4-bromothioanisole to precipitate out. The crystalline precipitate was collected by filtration and dried to give 158.4 g (0.78 mole, melting point 37.4–37.5° C.) of 4-bromothioanisole. The yield based on thioanisole was 78.0%. The purity of the 4-bromothioanisole obtained was not lower than 99.95% as determined by gas chromatography.

EXAMPLE 2

A one-liter four-necked flask equipped with a stirrer, thermometer, dropping funnel and Liebig condenser was charged with 124.2 g (1.00 mole) of thioanisole, and 0.13 g (0.001 mole) of aluminum chloride and 200 g of dichloromethane, and 160 g (1.0 mole) of bromine was added dropwise with stirring at 5° C. over 4 hours. Thereafter, the reaction was further allowed to proceed for 2 hours. After completion of the reaction, 50 g of water was added, and phase separation was effected, whereby a 4-bromothioanisole-containing organic layer was obtained. The dichloromethane was distilled off from the organic layer obtained, whereby 203.1 g of crude 4-bromothioanisolve was obtained. The purity of the thus-obtained crude 4-bromothioanisole was 90.1% as determined by gas chromatography.

A mixed solvent composed of methanol and water (60% (by weight) methanol) (300 g) was added to the crude 4-bromothioanisole obtained, and the resulting mixture was slowly cooled from 50° C. to −5° C. with stirring to thereby cause 4-bromothioanisole to precipitate out. The crystalline precipitate was collected by filtration. The crystals obtained were washed with methanol cooled at −5° C. and dried to give 154.8 g (0.762 mole) of 4-bromothioanisole. The yield based on thioanisole was 76.2%. The purity of the 4-bromothioanisole obtained was not lower than 99.95% as determined by gas chromatography.

EXAMPLE 3

A one-liter four-necked flask equipped with a stirrer, thermometer, dropping funnel and Liebig condenser was charged with 124.2 g (1.0 mole) of thioanisole and 0.068 g (0.001 mole) of boron trifluoride, and 160 g (1.0 mole) of bromine was added dropwise with stirring at 50° C. over 4 hours. Thereafter, the reaction was further allowed to proceed for 1 hour. After completion of the reaction, 50 g of water was added, and the organic layer was separated, whereby 203.9 g of crude 4-bromothioanisole was obtained. The purity of the thus-obtained crude 4-bromothioanisole was 90.5% as determined by gas chromatography.

Methanol (200.0 g) was added to the crude 4-bromothioanisole obtained, and the mixture was slowly cooled from 50° C. to −5° C. with stirring to thereby cause 4-bromothioanisole to precipitate out. The crystalline precipitate was collected by filtration and dried to give 159.5 g (0.785 mole) of 4-bromothioanisole. The yield based on thioanisole was 78.5%. The purity of the 4-bromothioanisole obtained was not lower than 99.95% as determined by gas chromatography.

COMPARATIVE EXAMPLE 1

A one-liter four-necked flask equipped with a stirrer, thermometer, dropping funnel and Liebig condenser was charged with 124.2 g (1.00 mole) of thioanisole and 0.32 g (0.002 mole) of iron(II) chloride, and 160.0 g (1.00 mole) of bromine was added dropwise with stirring at 50° C. over 4 hours. Thereafter, the reaction was further allowed to proceed for 1 hour. After completion of the reaction, 50 g of water was added, and the organic layer was separated, whereby 202.4 g of crude 4-bromothioanisole was obtained. The purity of the thus-obtained crude 4-bromothioanisole was 90.5% as determined by gas chromatography.

The thus-obtained crude 4-bromothioanisole was distilled in a Widmer distillation apparatus under reduced pressure to give 165.0 g of a fraction boiling at 103° C.–105° C. at 1,862 kPa. The fraction obtained was analyzed by gas chromatography, whereupon it was found to be a mixture of 94.8% of 4-bromothioanisole and 5.2% of 2-bromothioanisole.

COMPARATIVE EXAMPLE 2

A one-liter four-necked flask equipped with a stirrer, thermometer, dropping funnel and Liebig condenser was charged with 124.2 g (1.00 mole) of thioanisole and 0.32 g (0.002 mole) of iron(II) chloride, and 160.0 g (1.00 mole) of bromine was added dropwise with stirring at 50° C. over 4 hours. Thereafter, the reaction was further allowed to proceed for 1 hour. After completion of the reaction, 50 g of water was added, and the organic layer was separated, whereby 203.1 g of crude 4-bromothioanisole was obtained. The purity of the thus-obtained crude 4-bromothioanisole was 90.1% as determined by gas chromatography.

A mixed solvent composed of acetone and water (60% (by weight) acetone) (300.0 g) was added to the crude 4-bromothioanisole obtained, and the mixture was slowly cooled from 50° C. to −5° C. with stirring to thereby cause 4-bromothioanisole to precipitate out. The crystalline precipitate was collected by filtration and dried to give 55.0 g (0.27 mole) of 4-bromothioanisole. The yield based on thioanisole was 27.1%. The purity of the 4-bromothioanisole obtained was 98.2% as determined by gas chromatography.

INDUSTRIAL APPLICABILITY

According to the present invention, highly pure 4-bromothioanisole, which is a useful compound used in various fields such as the manufacture of medicinal chemicals, agrochemicals and functional materials, can be produced in a simple and industrially advantageous manner.

What is claimed is:

1. A process for producing 4-bromothioanisole which comprises the steps of:

reacting thioanisole with bromine to produce a mixture of 4-bromothioanisole and byproduct 2-bromothioanisole;

adding an alcoholic solvent to the mixture of 4-bromothioanisole and 2-bromothioanisole, wherein the alcoholic solvent is methanol or a mixed solvent composed of not less than 30% by weight of methanol and not more than 70% by weight of water;

cooling the mixture to a temperature of −20 to 30° C. to selectively crystallize 4-bromothioanisole; and isolating crystals of 4-bromothioanisole to separate 4-bromothioanisole from 2-bromothioanisole.

2. The process for producing 4-bromothioanisole according to claim 1, wherein the alcoholic solvent is added in an amount of 0.03 to 10 times the weight of 4-bromothioanisole.

3. The process for producing 4-bromothioanisole according to claim 1, wherein the mixed solvent contains not more than 50% by weight of water.

4. The process for producing 4-bromothioanisole according to claim 1, wherein the mixture is cooled to a temperature of −10 to 20° C. to selectively crystallize the 4-bromothioanisole.

* * * * *